United States Patent
Tkaczyk et al.

(10) Patent No.: US 7,613,274 B2
(45) Date of Patent: Nov. 3, 2009

(54) METHOD AND SYSTEM OF ENERGY INTEGRATING AND PHOTON COUNTING USING LAYERED PHOTON COUNTING DETECTOR

(75) Inventors: John Eric Tkaczyk, Delanson, NY (US); Jonathan D. Short, Saratoga Springs, NY (US); Yanfeng Du, Rexford, NY (US); Wen Li, Clifton Park, NY (US); Xiaoye Wu, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/941,175

(22) Filed: Nov. 16, 2007

(65) Prior Publication Data

US 2009/0129538 A1  May 21, 2009

(51) Int. Cl.
*G01N 23/00* (2006.01)
(52) U.S. Cl. ............................. 378/5; 378/19; 378/98.8
(58) Field of Classification Search ................... 378/5, 378/19, 98.8; 250/370.06, 370.09, 370.13
See application file for complete search history.

(56) References Cited

U.S. PATENT DOCUMENTS

| | | | |
|---|---|---|---|
| 4,511,799 A | 4/1985 | Bjorkholm | |
| 5,138,167 A * | 8/1992 | Barnes | 250/370.01 |
| 5,218,624 A | 6/1993 | LeMay | |
| 5,225,980 A | 7/1993 | Hsieh et al. | |
| 5,228,069 A | 7/1993 | Arenson et al. | |
| 5,262,871 A | 11/1993 | Wilder et al. | |
| 5,376,795 A | 12/1994 | Hasegawa et al. | |
| 5,400,378 A | 3/1995 | Toth | |
| 5,548,123 A | 8/1996 | Perez-Mendez et al. | |
| 5,789,737 A | 8/1998 | Street | |
| 6,198,790 B1 | 3/2001 | Pflaum | |
| 6,453,008 B1 | 9/2002 | Sakaguchi et al. | |
| 6,953,935 B1 | 10/2005 | Hoffman | |
| 7,092,481 B2 | 8/2006 | Hoffman | |
| 7,127,027 B2 | 10/2006 | Hoffman | |
| 7,209,536 B2 | 4/2007 | Walter et al. | |
| 7,260,174 B2 | 8/2007 | Hoffman et al. | |

(Continued)

OTHER PUBLICATIONS

Rashid-Farrokhi et al., "Local Tomography in Fan-Beam Geometry Using Wavelets," IEEE, 1996, 0-7803-3258-X/96, pp. 709-712.

(Continued)

*Primary Examiner*—Jurie Yun
(74) *Attorney, Agent, or Firm*—Patrick K. Patnode

(57) ABSTRACT

A diagnostic imaging system includes an x-ray source that emits a beam of x-ray energy toward an object to be imaged and an energy discriminating (ED) detector that receives the x-ray energy emitted by the x-ray energy source. The ED detector includes a first layer having a first thickness, wherein the first layer comprises a semiconductor configurable to operate in at least an integrating mode and a second layer having a second thickness greater than the first thickness, and configured to receive x-rays that pass through the first layer. The system further includes a data acquisition system (DAS) operably connected to the ED detector and a computer that is operably connected to the DAS. The computer is programmed to identify saturated data in the second layer and substitute the saturated data with non-saturated data from a corresponding pixel in the first layer.

20 Claims, 5 Drawing Sheets

FIG. 4

U.S. PATENT DOCUMENTS

| | | |
|---|---|---|
| 2002/0085664 A1 | 7/2002 | Bromberg et al. |
| 2002/0097320 A1 | 7/2002 | Zalis |
| 2003/0023163 A1 | 1/2003 | Johnson et al. |
| 2003/0031296 A1 | 2/2003 | Hoheisel |
| 2003/0113267 A1 | 6/2003 | Knopp et al. |
| 2003/0169847 A1 | 9/2003 | Karellas et al. |
| 2004/0136491 A1 | 7/2004 | Iatrou et al. |
| 2004/0202283 A1 | 10/2004 | Okumura et al. |
| 2004/0264627 A1 | 12/2004 | Besson |
| 2006/0109949 A1 | 5/2006 | Tkaczyk et al. |
| 2006/0109950 A1 | 5/2006 | Arenson et al. |

OTHER PUBLICATIONS

Sellin et al., "Characterisation of charge transport in compound semi-conductor detectors," Radiation Imaging Group, Department of Physics, University of Surrey, Guildford, UK.

"Direct vs. Indirect Conversion," Agfa.com, Dec. 1, 2006, http://www.agfa.com/en/he/knowledge_training/technology/direct_indirect_conversion/index.jsp.

Edling, "A pixel readout chip for medical X-ray imaging," Department of Radiation Sciences, Uppsala Universitet, Uppsala, Sweden.

"High Energy Particle/X-Ray Detector," Hamamatsu Photonics K.K., Solid State Division, Cat. No. KOTH0006E02, Nov. 2003, Hamamatsu City, Japan.

\* cited by examiner

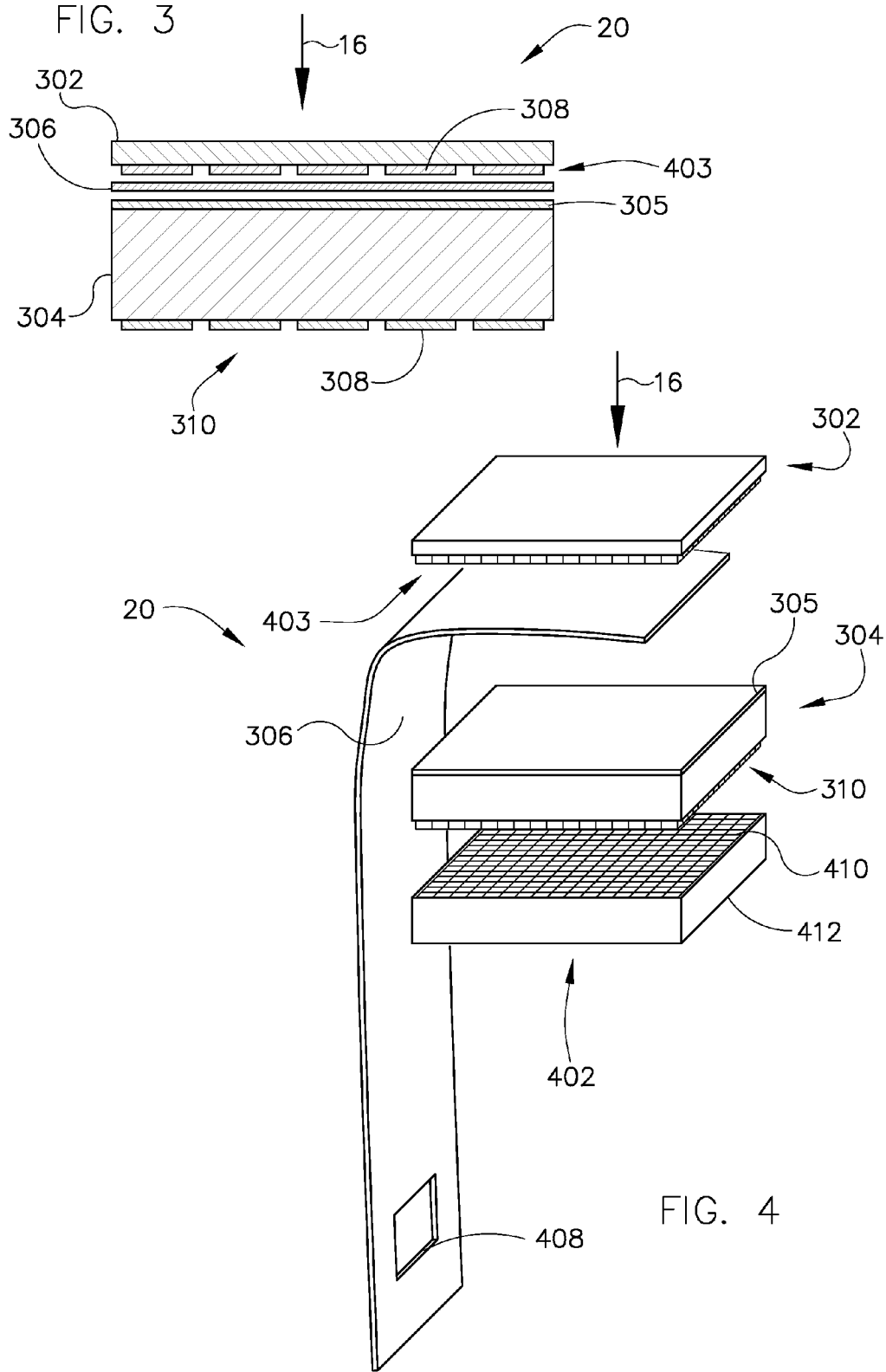

METHOD AND SYSTEM OF ENERGY INTEGRATING AND PHOTON COUNTING USING LAYERED PHOTON COUNTING DETECTOR

BACKGROUND OF THE INVENTION

The present invention relates generally to diagnostic imaging and, more particularly, to a method and apparatus for high flux rate imaging with energy discrimination, such as in computed tomography (CT) applications.

Diagnostics devices comprise x-ray systems, magnetic resonance (MR) systems, ultrasound systems, computed tomography (CT) systems, positron emission tomography (PET) systems, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photo-diodes for receiving the light energy from the adjacent scintillator and producing electrical signals therefrom.

Typically, each scintillator of a scintillator array converts x-rays to light energy. Each scintillator discharges light energy to a photodiode adjacent thereto. The photodiode detects the light energy and generates a corresponding electrical signal. The outputs of the photodiodes are then transmitted to the data processing system for image reconstruction. A characteristic of using scintillators and photodiodes is that the output signal passed to the system is proportional to the x-ray energy incident to the detector during an integration view time. Some systems provide, instead, a photon counting detection mechanism whereby the signal passed to the system is proportional to the number of x-ray photons incident to the detector during the integration view time. Since the spectrum of the incident x-ray flux has a breadth in energy, there is a considerable difference in the number of x-ray photons and the total energy of the photons. Thus, a photon counting detector has improved dose efficiency. In addition, the photon counting detector can be configured with additional energy thresholds to distinguish photons at different energy thresholds and count these in separate registers. Generally, photon counting systems used for CT imaging use direct conversion sensor materials because the signal charge created per x-ray is much greater than that of a scintillator/photodiode sensor.

A CT imaging system comprises an energy discriminating (ED) and/or multi energy (ME) CT imaging system that may be referred to as an EDCT and/or MECT imaging system. The EDCT and/or MECT imaging system may be configured to be responsive to different x-ray spectra. For example, a conventional third generation CT system acquires projections sequentially at different x-ray tube potentials. Two scans are acquired either back to back or interleaved in which the tube operates at 80 kVp and 160 kVp potentials. Special filters are placed between the x-ray source and the detector such that different detector rows collect projections of different x-ray energy spectra. The special filters that shape the x-ray spectrum in an example can be used for two scans that are acquired either back to back or interleaved. Energy sensitive detectors are used such that each x-ray photon reaching the detector is recorded with its photon energy.

Exemplary ways to obtain energy sensitive measurements comprise: (1) scan with two distinctive energy spectra, (2) detect photon energy according to the depth from the incident surface for energy deposition in the detector, and (3) photon counting with multiple energy thresholds. EDCT/MECT provides energy discrimination and material characterization. For example, in the absence of object scatter, the system derives the behavior at any other energy based on the signal from two regions of photon energy in the spectrum: the low-energy and the high-energy portions of the incident x-ray spectrum. In an energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two materials.

A conventional basis material decomposition (BMD) algorithm is based on the concept that in the energy region for medical CT, the x-ray attenuation of any given material can be represented by a proper density mix of two other materials, referred to as the basis materials. Based on the projections acquired at the two incident x-ray spectra, the BMD algorithm computes two sets of new projections, corresponding to two new CT images that each represents the equivalent density of one of the basis materials. Since a material density is independent of x-ray photon energy, these images are approximately free of beam-hardening artifacts. An operator can choose the basis material to target a certain material of interest, for example, to enhance the image contrast.

A previous photon counting detector saturates at high flux rate and degrades due to pile-up loss of detector quantum efficiency (DQE) and spectral information. Direct conversion semiconductor detectors that comprise high atomic number elements like cadmium telluride (CdTe) or cadmium zinc telluride (CZT) may suffer from polarization, for example, when operating in either the integration or photon counting mode. Other materials like silicon (Si) or gallium arsenide (GaAs) may have a crystal structure with fewer defects. These crystals may not polarize at high flux and have high mobility and therefore a high flux rate counting capability. Semiconductor layers such as silicon and GaAs may be employed as direct conversion radiation detectors operated in either the integration or photon counting mode. A thin layer of these low atomic number materials may not stop a substantial fraction of the flux. These materials as crystals provide low attenuation and stop a relatively small fraction of the photons in the beam of x-rays 16.

An energy discriminating (ED) detector may comprise a plurality of integrating layers. It is desirable for dose efficiency to have the total x-ray spectra that is incident to the detector to be absorbed in the combination of the layers. Conventionally, two scintillator/photodiode layers are used where the low energy portion of the spectra is absorbed in a thin top layer and high energy portion of the spectra is absorbed in a thick bottom layer. Top and bottom layers may, instead, comprise direct conversion layers, for example, with a relative thickness in a layer that may lead to polarization effects, instability, and/or non-linear responses at relatively high x-ray flux. Thick layers of direct conversion material require a longer transport distance for charge carriers and therefore a greater amount of charge trapping. An ED detector may comprise a plurality of scintillator and photodiode layers, for example, with interaction between the top and bottom layers that may add noise for the low and high energy signal.

Layered detectors may be challenging, difficult, and/or problematic, for example, because the ASIC parts, bonding pads, interconnect, and substrate materials between the top and bottom layers may attenuate the flux to the bottom layer without creating and/or contributing a signal that is employable and/or appropriate in image reconstruction. Coupling of the readout ASIC directly to the back of the top layer sensor may risk radiation damage to the ASIC and attenuation of the beam of x-rays 16 in traversal though the top layer to the bottom layer.

Alternately, an ED detector may comprise a single photon counting layer. At low incident flux, a single-layer, photon counting detector will generally give material basis decomposition at lower dose than the ED detector composed of multiple integrating layers. Such a layer needs to be thick enough such that it absorbs a substantial fraction of the incident x-ray flux. The relatively thick layer may lead to polarization effects, instability, and/or non-linear response at relatively high x-ray flux. Furthermore, a relatively thick, single layer photon counting detector will saturate due to pile-up when x-ray photons arrive at the detector faster than the readout electronics can register them.

Therefore, it would be desirable to design an apparatus and method to promote a reduction in one or more of energy discriminating (ED) detector layer thickness, ED detector polarization, instability, non-linearity, and/or noise. Further, it would be desirable to design an apparatus that has the improved dose efficiency of a photon counting system but that also has a means to mitigate the saturation phenomenon of pile-up.

BRIEF DESCRIPTION OF THE INVENTION

The invention in an implementation encompasses a CT system having an improved dose efficiency of a photon counting system and having a means to mitigate the saturation phenomenon of pile-up.

According to one aspect of the present invention, a diagnostic imaging system is disclosed that includes an x-ray source that emits a beam of x-ray energy toward an object to be imaged and an energy discriminating (ED) detector that receives the x-ray energy emitted by the x-ray energy source. The ED detector includes a first layer having a first thickness, wherein the first layer comprises a semiconductor configurable to operate in at least an integrating mode and a second layer having a second thickness greater than the first thickness, and configured to receive x-rays that pass through the first layer. The system further includes a data acquisition system (DAS) operably connected to the ED detector and a computer that is operably connected to the DAS. The computer is programmed to identify saturated data in the second layer and substitute the saturated data with non-saturated data from a corresponding pixel in the first layer.

According to another aspect of the present invention, a method of diagnostic imaging includes projecting a beam of x-ray energy toward an object to be imaged, positioning a first layer of an energy discriminating (ED) detector comprising a semiconductor configurable to operate in at least an integrating mode, to receive x-rays that pass through the object, and acquiring x-ray data in the first layer from the x-rays passing through the object. The method further includes positioning a second layer of the ED detector having a thickness greater than the first layer, to receive x-rays that pass through the first layer, directly converting incident photons to electrical charge within the second layer, identifying saturated data within the second layer, and replacing the saturated data with non-saturated data acquired in the first layer.

According to yet another aspect of the present invention, a diagnostic imaging detector includes a stacked arrangement of a direct conversion sensor and a sensor configurable to operate in at least an integrating mode, wherein the configurable sensor is positioned between an x-ray source and the direct conversion sensor, and wherein the direct conversion sensor has a thickness greater than a thickness of the configurable sensor, wherein the direct conversion sensor has a saturation threshold in an electromagnetic range of the x-ray source, wherein the configurable sensor has a saturation threshold greater than the saturation threshold of the direct conversion sensor and outputs unsaturated imaging data acquired in an x-ray energy range above the saturation threshold of the direct conversion sensor, and wherein saturated data in the direct conversion layer is substituted with non-saturated data from a corresponding pixel in the configurable sensor.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 3 is a cross-sectional view of an energy discriminating (ED) detector having an integrating sensor and a direct conversion sensor according to an embodiment of the present invention.

FIG. 4 is a perspective view of the ED detector of FIG. 3 having a first indirect conversion layer and a second direct conversion layer according to an embodiment of the present invention.

DETAILED DESCRIPTION OF THE PREFERRED EMBODIMENT

Diagnostics devices typically comprise x-ray systems, magnetic resonance (MR) systems, ultrasound systems, computed tomography (CT) systems, positron emission tomography (PET) systems, and other types of imaging systems.

Applications of x-ray sources comprise imaging, medical, security, and industrial inspection applications. The operating environment described herein includes a 64-slice CT system. However, it will be appreciated by those skilled in the art that an implementation is also applicable for use with single-slice or other multi-slice configurations. More generally, an implementation is employable for detection and conversion of x-rays. However, one skilled in the art will further appreciate that an implementation is employable for the detection and conversion of other high frequency electromagnetic energy, high frequency polychromatic electromagnetic energy, and/or radiographic energy. An implementation is employable with a "third generation" CT scanner and/or other CT systems.

Figure 1:
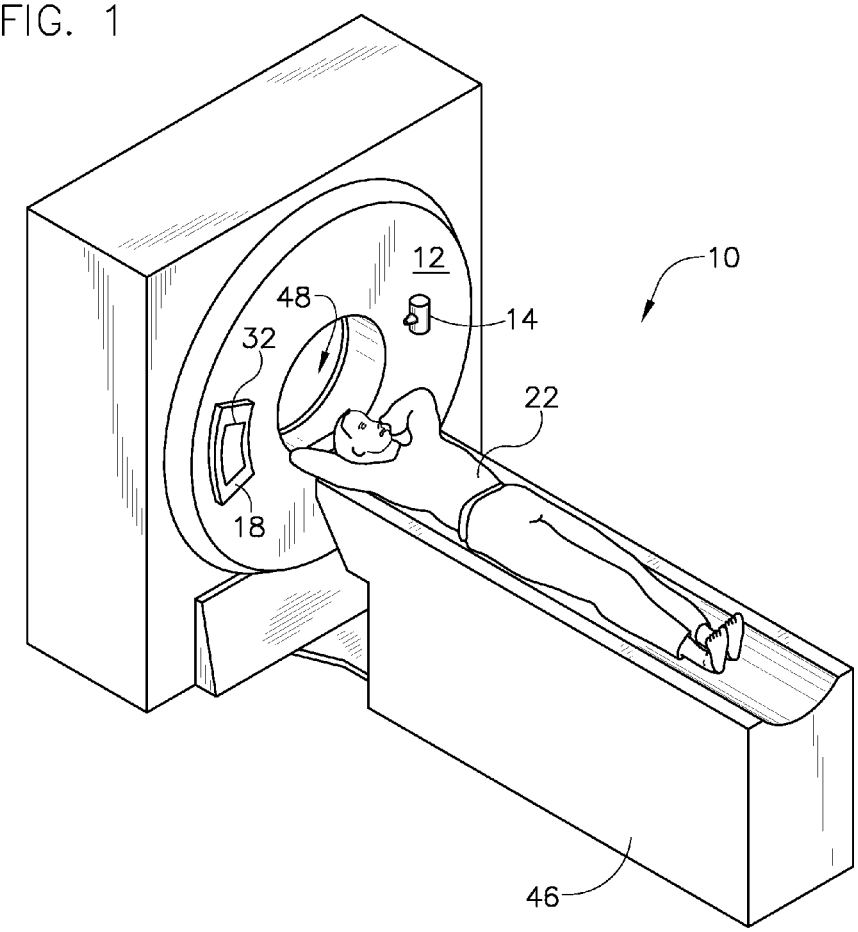
FIG. 1 is a pictorial view of an implementation of a CT imaging system.
Figure 2:
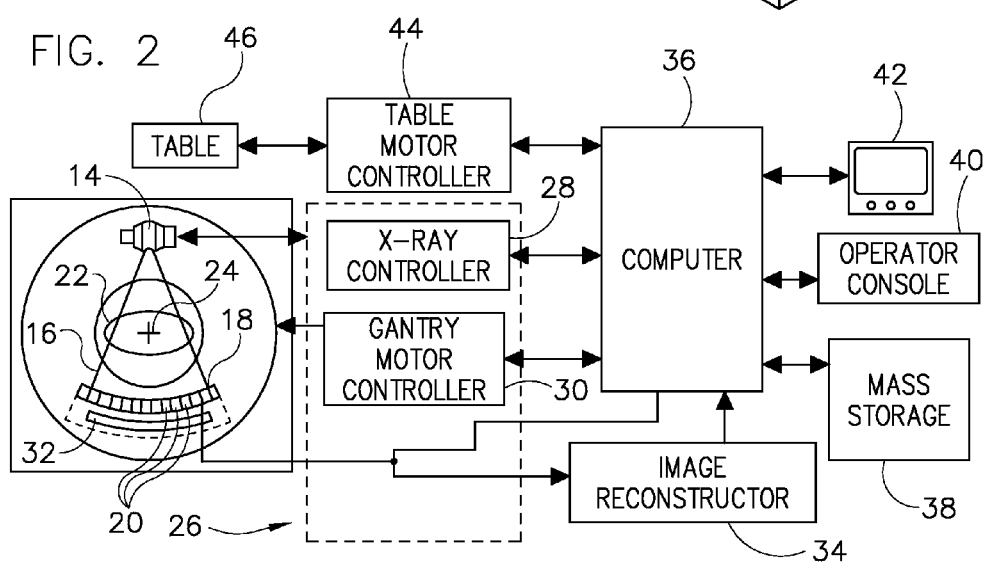
FIG. 2 is a block schematic diagram of an implementation of the system of FIG. 1.

Referring to FIGS. 1 and 2, a diagnostic and/or computed tomography (CT) imaging system 10 is shown as including a gantry 12 representative of a "third generation" CT scanner. The CT imaging system 10 in an example comprises an energy discriminating (ED) and/or multi energy (ME) CT imaging system that may be referred to as an EDCT and/or MECT imaging system. Gantry 12 has an x-ray source 14 that projects a beam of x-rays 16 toward a detector array 18 on the opposite side of the gantry 12. Detector array 18 is formed by a plurality of detectors such as energy discriminating (ED) detectors 20 which together sense the projected x-rays that pass through a medical patient 22. Each ED detector 20 produces an electrical signal that represents the intensity of an impinging x-ray beam and hence the attenuated beam as it passes through the patient 22. The ED detector 20 obtains ED readout from the beam of x-rays 16. During a scan to acquire x-ray projection data, gantry 12 and the components mounted thereon rotate about a center of rotation 24, as will be appreciated by those skilled in the art.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from the ED detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

EDCT/MECT provides energy discrimination and material characterization. For example, in the absence of object scatter, the system derives the behavior at any other energy based on the signal from two regions of photon energy in the spectrum: the low-energy and the high-energy portions of the incident x-ray spectrum. In an energy region of CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object 22 composed of two materials.

In one embodiment, photon counting with enhanced energy separation, and/or extended dynamic range is provided. A configurable implementation of the ED detector 20 comprises photon counting at low flux and/or count rate and switchability to an integration mode at high flux and/or count rate. One implementation comprises a material with extended range and coupled to a DAS 32 that can read out both photon counting and integration information. An exemplary implementation of the ED detector 20 comprises photon counting and energy integration capability such as for x-ray and CT systems for imaging in medical, industrial, and/or security systems.

An implementation of the ED detector 20 includes photon counting employable for x-ray radiography and/or CT; an upstream, top, first, integrating, and/or configurable layer, detector, and/or sensor employable to stop a small, reduced, and/or minor fraction of the incident flux; and a downstream, bottom, second, photon counting, and/or energy binning layer, detector, and/or sensor employable to stop a substantial, majority, and/or most amount of flux. An implementation of an upstream layer includes a thin silicon diode or thin film scintillator plus photodiode sensor. A scintillator may be vapor deposited or screen printed as a uniform layer or pattered layer. The operation of a photodiode alone or in combination with a scintillator is to convert x-rays to an integrated charge signal on an array of pixel areas. The interaction of an x-ray with the photodiode or scintillator material results in free charges that are collected by the photodiode contacts and readout by the DAS as a signal charge proportional to the x-ray energy. The photodiode as known in the art includes an array of electrical contacts on one surface which define an array of collecting pixel areas and another set of contacts setting up the electric field condition within the device. Typically the contacts are made on one surface of the photodiode layer. The pixel contacts can be the anode or cathode depending on the type of semiconductor utilized, either electron or hole transport dominated. The photodiode has regions within each pixel area doped with secondary elements to create electric fields that sweep free charge to the pixel contacts even in the absence of a bias voltage across the anode-cathode contacts. The photodiode is operated with applied voltage typically less than 30 volts in reverse of the diode or typically zero volts across the anode-cathode contacts.

A second implementation of an upstream layer includes a thin semiconductor material operated as a direct conversion sensor. The interaction of an x-ray with the semiconductor material results in free charges that are collected by the pixel contacts and readout by the DAS. The operation of the direct conversion sensor is to convert x-rays to an integrated and/or photon count signal on an array of pixel areas. The direct conversion sensor as known in the art includes an array of electrical contacts on one surface which define an array of collecting pixel areas and another common electrode on the opposite surface setting up the electric field within the device. A sufficient voltage bias is applied across the anode-cathode contacts to ensure efficient collection of free charge created within the device due to the interaction of x-rays with the direct conversion material. Typically, the voltage is applied to create an internal electric field sufficient to collect signal charge at the pixel contacts. At low flux rate the first layer can suffer from electronic noise degradation.

Referring to FIGS. 3 and 4, an ED detector 20 comprises a plurality of layers, for example, an upstream first layer 302, a downstream second layer 304, and a plurality of connectors, such as connectors 306, 402. The first layer 302 and the second layer 304 include a plurality of contacts, detection and/or conversion elements, electronically pixelated structures, or pixels 308. One or more electronic pixelations may be accomplished and/or implemented through application and/or employment of two-dimensional (2D) arrays and/or arrangements 310, 403 of pixels 308 onto semiconductor layers of the first layer 302 and the second layer 304. Pixelation may be defined two-dimensionally across the width and length of the semiconductor layers of the first layer 302 and the second layer 304.

The first layer 302 includes an indirect conversion layer reading out an integration signal that may include, for example, an array of frontlit or backlit photodiodes, optionally optically coupled to a thin scintillator layer. The first layer 302 operates at high flux, whereas a photon counting layer such as the second layer 304 would saturate above 1E7 counts per second per millimeter squared. An integration sensor may be operated to the limits of the unattenuated source flux, typically 5E9 counts per second per millimeter squared, or higher. The first layer 302 typically operates without experiencing a saturation condition and may provide data for the formation of an image even if the data from the second layer is not available (i.e., saturated). A material for the first layer 302 may include a semiconductor, monolithic semiconductor crystal, silicon (Si), gallium arsenide (GaAs), and/or a low atomic number material, and may have a thickness of typically 0.02 mm to 2.5 mm. In one embodiment of the invention the atomic number may be in a range of about 14 to about 64.

The second layer 304 includes typically a direct conversion layer such as a photon counting and/or thick sensor that comprises a cathode 305 and an arrangement 310 of pixels 308 as an anode. The second layer 304 is configurable as it provides photon counting and/or charge integration data for the reconstruction of the image. The availability of both photon counting and integration data provides for greater operating dynamic range in that the preferred photon counting signal can be utilized for image formation at low incident flux rate whereas the integration signal is available at high flux rate. In another example, the second layer 304 is non-configurable in that it provides only for photon counting signals, which may be available at incident flux rates below a threshold level. The second layer 304 may operate in a photon counting mode at low flux rate at, for example, below 1E7 counts per sec per millimeter squared. In a further example, the second layer 304 may provide energy information at multiple energy thresholds available for a photon counting detector at low flux rate, for example, information employable for energy discrimination in image reconstruction of the object 22. In one implementation, the second layer 304 may have an increased saturation flux by being operated in a photon counting mode.

A material for the second layer 304 comprises a high atomic number and high density semiconductor, monolithic semiconductor crystal, with good x-ray stopping power like cadmium telluride (CdTe), cadmium zinc telluride (CZT), and/or high atomic number material. In a general flow direction of the beam of x-rays 16, the second layer 304 comprises an exemplary thickness of 3.0 mm, and may typically range from 2.0 mm to 7.0 mm. An arrangement 310 of pixels 308 as the anode of the second layer 304 may comprise an anode and grid bias connection.

The connector 306 may provide high voltage distribution, isolation, biasing, and/or flexible connector, for example, to ASICs (application specific integrated circuits) 408 of the DAS 32. The array of photodiodes in the first layer 302 may be typically unbiased with no voltage across the array. As such, charge collected when photons interact with the photodiodes such as in the first layer 302 may flow out of the contacts 308 as a result of diffusion and electric fields that are built into the device. The connector 402 comprises two-sided packaging that includes an arrangement and/or pixel array 410 and a photon-counting ASIC 412 of the DAS 32. Pixel array 410, as an example, may include a sixteen-by-sixteen bump bond array with 1.0 mm pitch. One skilled in the art would recognize that other electronic pixelations may be accomplished and/or implemented through application and/or employment of two-dimensional (2D) arrays of pixels 308 as the pixel array 410 on the two sided packaging of the connector 402. Pixelation may be defined two-dimensionally across the width and length of two sided packaging of the connector 402.

The first layer 302 typically stops no more than 50% of the flux and may stop less than 20% of the flux. The dual layer concept described herein operates even with stopping as little as 1% flux in the first layer 302. For example, at 1% absorption in the top layer, a signal-to-noise ratio (SNR) at 1E8 counts per second per millimeter squared will be the same as at 1E6 counts per second per millimeter squared when both layers 302, 304 are providing valid data.

Figure 5:
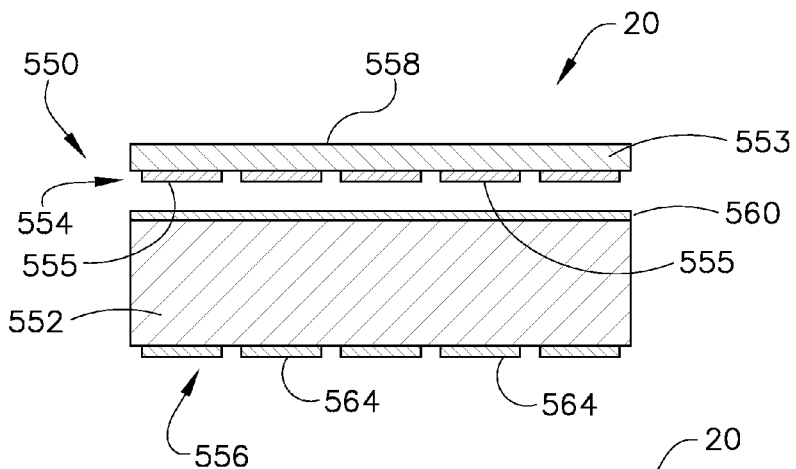
FIG. 5 is a cross-sectional view of an ED detector having two direct conversion sensors according to an embodiment of the present invention.
Figure 6:
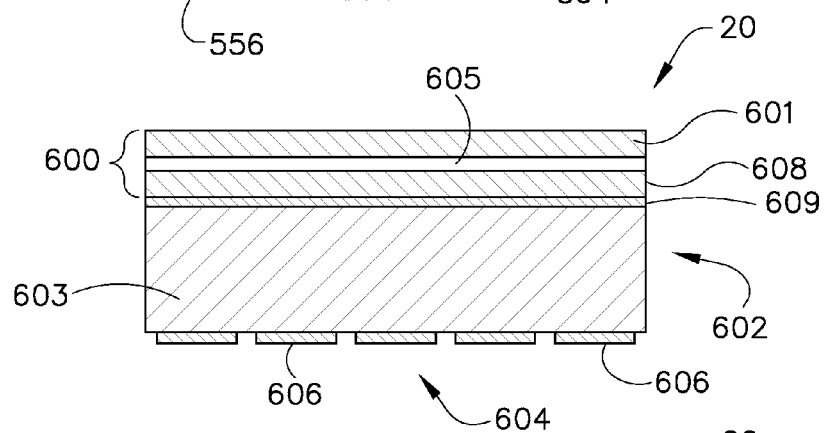
FIG. 6 is a cross-sectional view of an ED detector having a vapor deposited scintillator and a direct conversion sensor according to an embodiment of the present invention.
Figure 7:
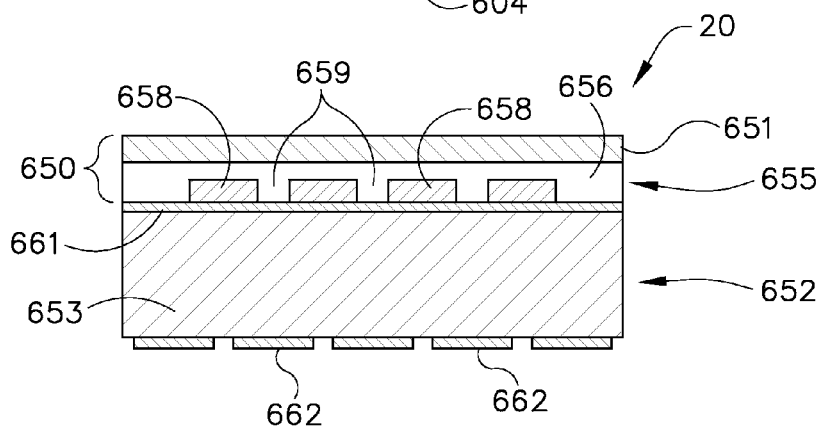
FIG. 7 is a cross-sectional view of an ED detector having a segmented scintillator and a direct conversion sensor according to an embodiment of the present invention.

FIGS. 5-7 illustrate variations of the ED detector 20 according to embodiments of the present invention. In the embodiments described herein, a first layer is configured to operate in integrating mode and a second layer is configured to operate in photon counting mode.

Referring now to FIG. 5, an ED detector 20 comprises a plurality of layers, for example, an upstream first layer 550 and a downstream second layer 552. In this embodiment, both the first layer 550 and the second layer 552 include a direct conversion material. Pixelation in each layer 550, 552 may be accomplished and/or implemented through application of two-dimensional (2D) arrays 554, 556 of pixels 555, 564 onto semiconductor layers of the first layer 550 and the second layer 552. Pixelation may be defined two-dimensionally across the width and length of the semiconductor layers of the first layer 550 and the second layer 552.

The first layer 550 includes a direct conversion layer that can be operated in a photon counting or configurable mode, depending on the type of DAS ASIC that is connected to the sensor. The first layer 550 typically operates without experiencing a saturation condition and may provide data for the formation of an image even if the data from the second layer is not available (i.e., saturated). A material 553 for the first layer 550 typically includes a low attenuation sensor such as silicon or gallium arsenide (GaAs). The use of silicon allows stable and reproducible operation at wide dynamic range in both modes because of its high quality crystal structure. Furthermore, the direct conversion of x-rays in the silicon generates enough charge to read out photons directly in either a photon counting mode with energy binning, or with a configurable mode. The first layer 550 typically includes a cathode 558 and an arrangement 554 of pixels 555 as an anode.

The second layer 552 likewise includes a direct conversion layer such as a photon counting and/or thick sensor that comprises a cathode 560 and an array 556 of pixels 564 as an anode. The second layer 552 is configurable and provides photon counting and/or charge integration data for the reconstruction of the image. A material for the second layer 552 comprises a high atomic number and high density semiconductor, monolithic semiconductor crystal, with good x-ray stopping power like cadmium telluride (CdTe), cadmium zinc telluride (CZT), and/or high atomic number material. The second layer 552 comprises a thickness of 3.0 mm, and may typically range from 2.0 mm to 7.0 mm.

Referring now to FIG. 6, an ED detector 20 comprises a plurality of layers, for example, an upstream first layer 600 and a downstream second layer 602. In this embodiment the first layer 600 includes a thin photodiode integrating sensor 601 and a scintillator 608, and the second layer 602 includes a direct conversion material 603. The scintillator 608 is attached to the photodiode 601 via an optically transparent adhesive 605 and may be vapor deposited or screen printed directly onto the photodiode 601. The scintillator 608, positioned as such, may serve to electrically isolate the photodiode 601 from the second layer 602. However, one skilled in the art would recognize that an additional insulating layer 609, may be positioned to provide additional electrical insulation between the first and second layers 600, 602.

A material for the photodiode 601 of the first layer 600 may include a semiconductor, monolithic semiconductor crystal, silicon (Si), gallium arsenide (GaAs), and/or a low atomic number material, and may have a thickness of typically 0.02 mm to 2.5 mm. The vapor deposited material for the scintillator 608 within the first layer 600 may include CsI or other scintillating materials as is commonly understood within the art. Additionally, because the scintillator 608 is thin (typically from a few hundred microns to a millimeter in thickness), the scintillator 608 need not be segmented or pixelated when applied to the surface of the photodiode 601.

Pixelation in the second layer 602 may be accomplished with a two-dimensional (2D) array 604 of pixels 606 on a semiconductor layer 603 of the second layer 602. Pixelation may be defined two-dimensionally across the width and length of the semiconductor layers of the second layer 602.

Photodiode 601 is configured to integrate a signal and typically operates without experiencing a saturation condition. The first layer 600 may provide data for the formation of an image even if the data from the second layer 602 is not available (i.e., saturated). The second layer 602 includes a direct conversion layer 603 such as a photon counting and/or thick sensor that comprises a cathode 609 and an arrangement 604 of pixels 606 as an anode. The second layer 602 is configurable and provides photon counting and/or charge integration data for the reconstruction of the image. A material for the second layer 602 comprises a high atomic number and high density semiconductor, monolithic semiconductor crystal, with good x-ray stopping power like cadmium telluride (CdTe), cadmium zinc telluride (CZT), and/or high atomic number material. The second layer 602 comprises a thickness of 3.0 mm, and may typically range from 2.0 mm to 7.0 mm.

Referring now to FIG. 7, an ED detector 20 comprises a plurality of layers including an upstream first layer 650 and a downstream second layer 652. The first layer 650 includes a thin photodiode integrating sensor 651. However, in this embodiment, a scintillator 655 includes a plurality of segmented scintillators 658 having gaps 659 therebetween. The second layer 652 includes a direct conversion material 653. The segmented scintillators 658 are attached to the photodiode 651 via an optically transparent adhesive 656 and may be vapor deposited or screen printed directly onto the photodiode. The scintillators 658, positioned as such, may serve to electrically isolate the photodiode 651 from the second layer 652. However, one skilled in the art would recognize that an additional insulating layer 661, may be positioned therebetween to provide additional electrical insulation between the first and second layers 650, 652.

The segmented scintillators 658 allow for a hybrid design where high and low filtration is provided on neighboring regions, thus providing effective flux management. More specifically, x-rays that pass through each scintillator 658 are filtered more than x-rays that pass through the gaps 659. Thus, an integration signal is obtained in the segmented scintillators 658, and because the x-rays passing therethrough are filtered, an extended dynamic range is available in the second layer 652. Additionally, x-rays that pass through the gaps 659, being substantially less filtered than those passing through the scintillators 658, provide high fidelity photon counting in the second layer 652. One skilled in the art would recognize that the embodiment described with respect to FIG. 7 may include a pattern of segmented scintillators 658 that is different from a pattern of anode contacts 662 of the second layer 652, or that the pattern of segmented scintillators 658 may be substantially the same as the pattern of anode contacts 662.

Figure 8:
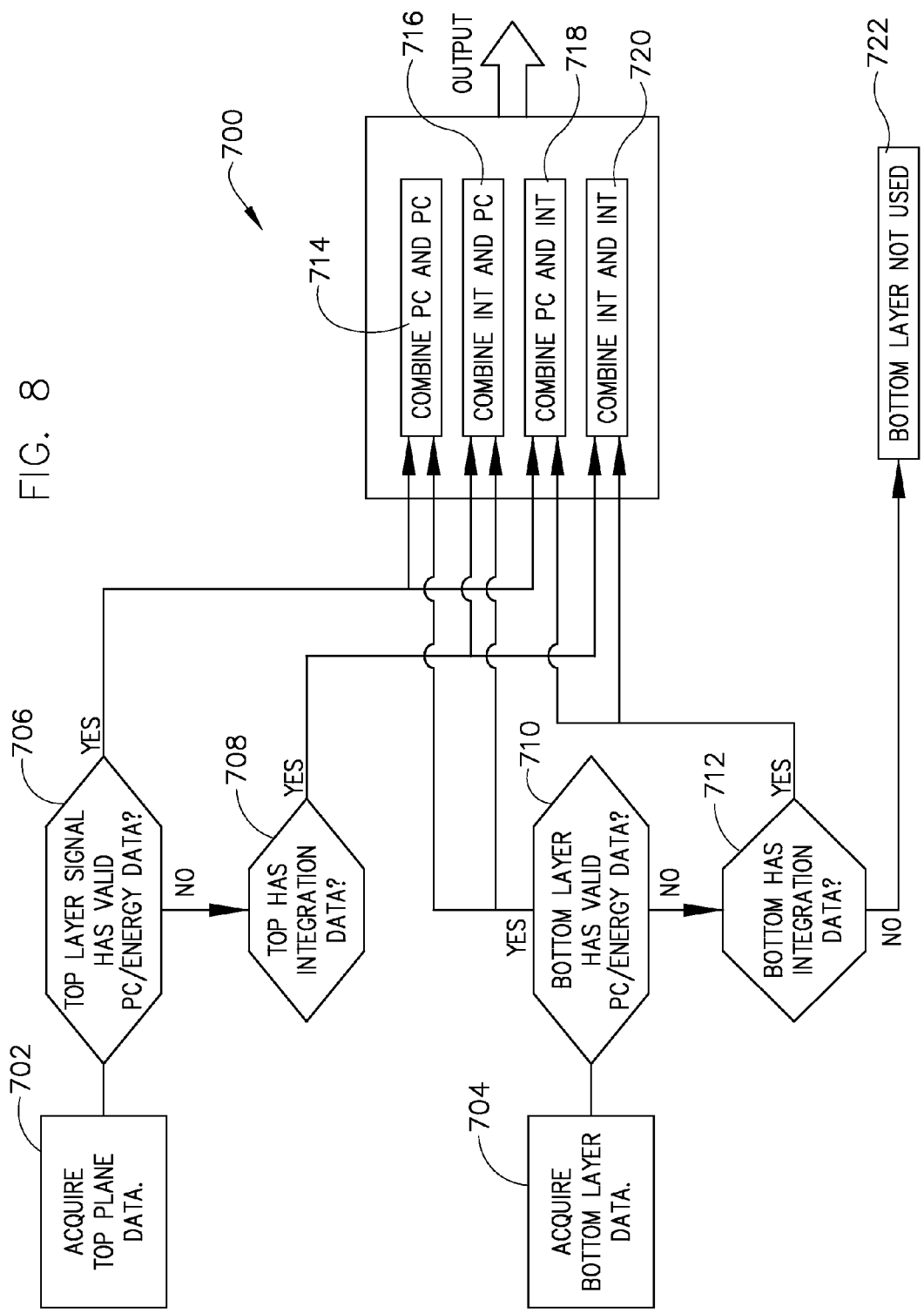
FIG. 8 is a flowchart for readout of a ED detector according to an embodiment of the present invention.

FIG. 8 illustrates a strategy 700 for acquiring data in and combining data from the top and bottom layers of the embodiments described herein. According to strategy 700, data is acquired in the top layer at 702 and in the bottom layer at 704. The top layer is assessed at 706 for valid energy or photon counting (PC) data, and if the top layer does not have valid PC data, then the top layer is determined to have integration data at 708. The bottom layer is assessed at 710 for valid PC data, and, if the bottom layer does not have valid PC data, then the bottom layer is further assessed at 712 for integration data as well.

As such, the strategy 700 provides optimal use of a two-layer ED detector as described in embodiments herein. Specifically, a highest level of energy resolution and fidelity is achieved at 714 where PC data is acquired from both layers of a two-layer design. At higher flux, however, PC data may not be available, due to detector saturation, in one of the first and second layers of the ED detector. As such, at 716 and 718 integration data from one layer may be combined with PC data of the other layer. At still higher flux rates, both the top and bottom detectors may not contain valid PC data, yet both may provide valid integration data. Thus, at 720, integration data from both the top and bottom layers may be combined to provide energy discriminating data. Finally, at still a higher flux rate, the bottom layer may saturate, even during operation in integration mode. Thus, at 722, the bottom layer is not used for providing imaging data and non-ED (integrating) data is obtained from the top layer only. One skilled in the art will recognize that, at lower flux levels, increased fidelity will be obtained by the use of strategy 700. Furthermore, as the flux level increases and saturation occurs in one of the layers, ED data may be obtained despite saturation occurring. Finally, as the flux level increases to very high levels, to the extent that the bottom layer is not used, one skilled in the art will recognize that valid data may be obtained in the first layer, though the data obtained will not provide an ED capability.

Figure 9:
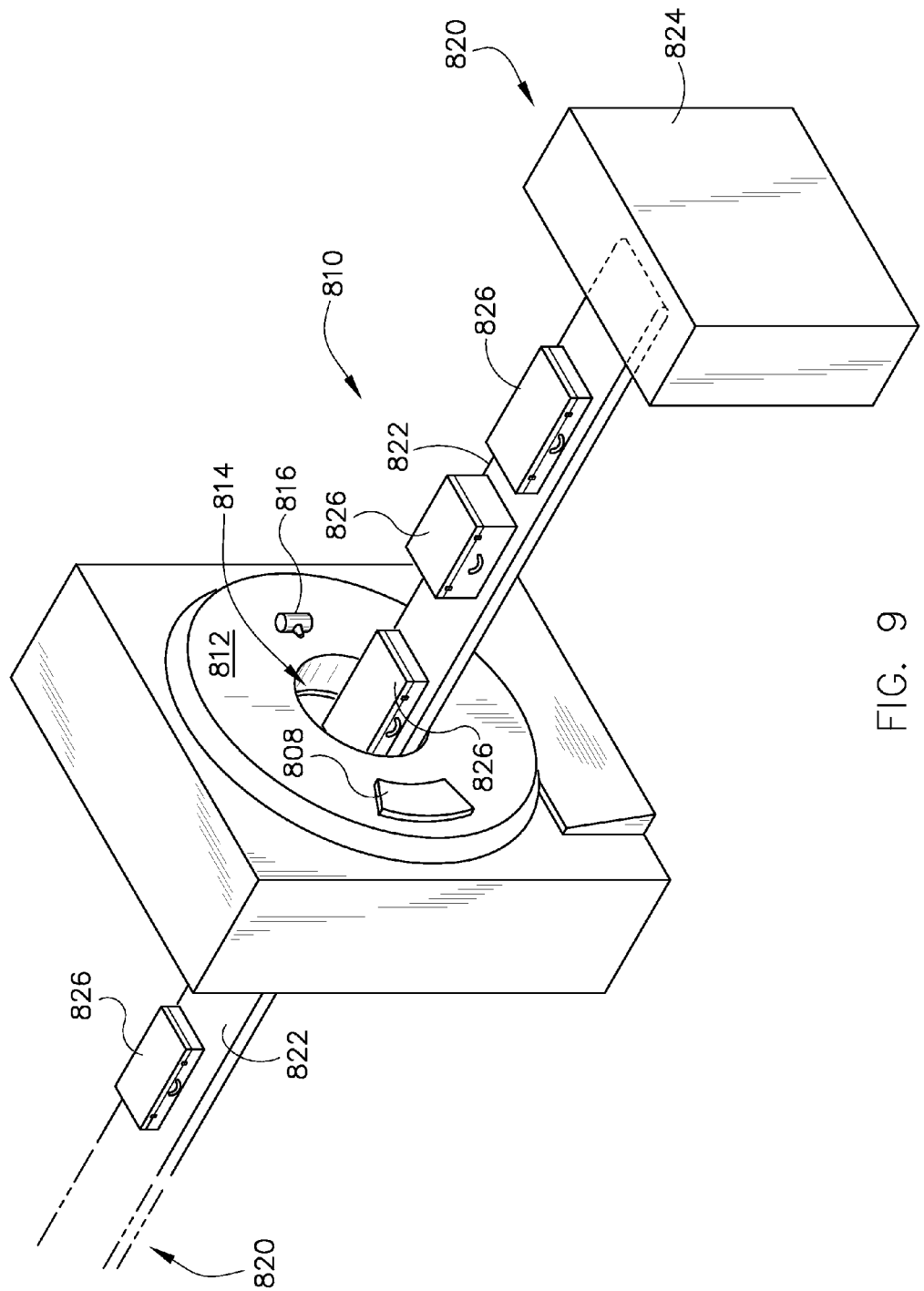
FIG. 9 is a pictorial view of a CT system for use with a non-invasive package inspection system.

Referring now to FIG. 9, package/baggage inspection system 810 includes a rotatable gantry 812 having an opening 814 therein through which packages or pieces of baggage may pass. The rotatable gantry 812 houses an x-ray and/or high frequency electromagnetic energy source 816 as well as a detector assembly 808 having scintillator arrays comprised of scintillator cells. A conveyor system 820 is also provided and includes a conveyor belt 822 supported by structure 824 to automatically and continuously pass packages or baggage pieces 826 through opening 814 to be scanned. Objects 826 are fed through opening 814 by conveyor belt 822, imaging data is then acquired, and the conveyor belt 822 removes the packages 826 from opening 814 in a controlled and continuous manner. As a result, postal inspectors, baggage handlers, and other security personnel may non-invasively inspect the contents of packages 826 for explosives, knives, guns, contraband, etc.

An implementation of the system 10 and/or 100 in an example comprises a plurality of components such as one or more of electronic components, hardware components, and/or computer software components. A number of such components can be combined or divided in an implementation of the system 10 and/or 100. An exemplary component of an implementation of the system 10 and/or 100 employs and/or comprises a set and/or series of computer instructions written in or implemented with any of a number of programming languages, as will be appreciated by those skilled in the art. An exemplary technical effect is one or more exemplary and/or desirable functions, approaches, and/or procedures. An implementation of the system 10 and/or 100 in an example comprises any (e.g., horizontal, oblique, or vertical) orientation, with the description and figures herein illustrating an exemplary orientation of an implementation of the system 10 and/or 100, for explanatory purposes.

An implementation of the system 10 and/or the system 100 encompasses an article. The article comprises one or more computer-readable signal-bearing media. The article comprises means in the one or more media for one or more exemplary and/or desirable functions, approaches, and/or procedures. An example of the system 10 and/or the system 100 employs one or more computer readable signal bearing media. A computer-readable signal-bearing medium stores software, firmware and/or assembly language for performing one or more portions of one or more implementations. A computer-readable signal bearing medium for an implementation of the system 10 and/or the system 100 comprises the recordable data storage medium of the image reconstructor 34, and/or the mass storage device 38 of the computer 36. A computer-readable signal-bearing medium for an implementation of the system 10 and/or the system 100 comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 100, for instance, one or more of a telephone network, a local area network ("LAN"), a wide area network ("WAN"), the Internet, and/or a wireless network.

Therefore, according to an embodiment of the present invention, a diagnostic imaging system includes an x-ray source that emits a beam of x-ray energy toward an object to be imaged and an energy discriminating (ED) detector that receives the x-ray energy emitted by the x-ray energy source. The ED detector includes a first layer having a first thickness, wherein the first layer comprises a semiconductor configurable to operate in at least an integrating mode and a second layer having a second thickness greater than the first thickness, and configured to receive x-rays that pass through the first layer. The system further includes a data acquisition system (DAS) operably connected to the ED detector and a computer that is operably connected to the DAS. The computer is programmed to identify saturated data in the second layer and substitute the saturated data with non-saturated data from a corresponding pixel in the first layer.

According to another embodiment of the present invention, a method of diagnostic imaging includes projecting a beam of x-ray energy toward an object to be imaged, positioning a first layer of an energy discriminating (ED) detector comprising a semiconductor configurable to operate in at least an integrating mode, to receive x-rays that pass through the object, and acquiring x-ray data in the first layer from the x-rays passing through the object. The method further includes positioning a second layer of the ED detector having a thickness greater than the first layer, to receive x-rays that pass through the first layer, directly converting incident photons to electrical charge within the second layer, identifying saturated data within the second layer, and replacing the saturated data with non-saturated data acquired in the first layer.

According to yet another embodiment of the present invention, a diagnostic imaging detector includes a stacked arrangement of a direct conversion sensor and a sensor configurable to operate in at least an integrating mode, wherein the configurable sensor is positioned between an x-ray source and the direct conversion sensor, and wherein the direct conversion sensor has a thickness greater than a thickness of the configurable sensor, wherein the direct conversion sensor has a saturation threshold in an electromagnetic range of the x-ray source, wherein the configurable sensor has a saturation threshold greater than the saturation threshold of the direct conversion sensor and outputs unsaturated imaging data acquired in an x-ray energy range above the saturation threshold of the direct conversion sensor, and wherein saturated data in the direct conversion layer is substituted with non-saturated data from a corresponding pixel in the configurable sensor.

The steps or operations described herein are examples. There may be variations to these steps or operations without departing from the spirit of the invention. For example, the steps may be performed in a differing order, or steps may be added, deleted, or modified.

The present invention has been described in terms of the preferred embodiment, and it is recognized that equivalents, alternatives, and modifications, aside from those expressly stated, are possible and within the scope of the appending claims.

What is claimed is:

1. A diagnostic imaging system comprising:
   an x-ray source that emits a beam of x-ray energy toward an object to be imaged;
   an energy discriminating (ED) detector that receives the x-ray energy emitted by the x-ray energy source, wherein the ED detector comprises:
      a first layer having a first thickness, wherein the first layer comprises a semiconductor configurable to operate in at least an integrating mode, further wherein the first layer comprises a material having a low atomic number; and
      a second layer having a second thickness greater than the first thickness, and configured to receive x-rays that pass through the first layer; and
   a data acquisition system (DAS) operably connected to the ED detector; and
   a computer operably connected to the DAS, wherein the computer is programmed to:
      identify saturated data in the second layer; and
      substitute the saturated data with non-saturated data from a corresponding pixel in the first layer.

2. The diagnostic imaging system of claim 1 wherein the first layer is configurable to operate also in photon-counting mode.

3. The diagnostic imaging system of claim 1 wherein the first layer comprises an indirect conversion detector.

4. The diagnostic imaging system of claim 3 wherein the first layer comprises a photodiode and a scintillator.

5. The diagnostic imaging system of claim 4 wherein the photodiode is one of a front lit and a back lit photodiode.

6. The diagnostic imaging system of claim 3 wherein the second layer comprises a direct conversion photon counting layer.

7. The diagnostic imaging system of claim 1 wherein the second layer is operable in any one of a photon counting mode and an integrating mode.

8. The diagnostic imaging system of claim 1 wherein the first layer is configured to attenuate a first percentage of incident photons of the beam of x-ray energy emitted by the x-ray source, and the second layer is configured to attenuate a second percentage of the incident photons, wherein the second percentage is greater than the first percentage.

9. The diagnostic imaging system of claim I wherein the first layer comprises a material with an atomic number in a range of about 14 to about 64.

10. The diagnostic imaging system of claim 1 wherein the first layer comprises silicon (Si) or gallium arsenide (GaAs).

11. A method of diagnostic imaging comprising:
projecting a beam of x-ray energy toward an object to be imaged;
positioning a first layer of an energy discriminating (ED) detector comprising a semiconductor configurable to operate in at least an integrating mode, to receive x-rays that pass through the object;
acquiring x-ray data in the first layer from the x-rays passing through the object;
positioning a second layer of the ED detector having a thickness greater than the first layer, to receive x-rays that pass through the first layer, further wherein a material of the second layer is different than a material of the first layer;
directly converting incident photons to electrical charge within the second layer;
identifying saturated data within the second layer; and
replacing the saturated data with non-saturated data acquired in the first layer.

12. The method of claim 11 further comprising operating the first layer in one of a photon counting mode and an integrating mode.

13. The method of claim 11 further comprising operating the second layer in one of a photon counting mode and an integrating mode.

14. The method of claim 11 further comprising attenuating up to fifty percent of the incident photons within the first layer, wherein the first layer comprises at least one of silicon (Si) and gallium arsenide (GaAs).

15. A diagnostic imaging detector comprising:
a stacked arrangement of a direct conversion sensor and a sensor configurable to operate in at least an integrating mode, wherein the configurable sensor is positioned between an x-ray source and the direct conversion sensor, and wherein the direct conversion sensor has a thickness greater than a thickness of the configurable sensor, wherein a material of the configurable sensor has an atomic number lower than an atomic number of a material of the direct conversion sensor;
wherein the direct conversion sensor has a saturation threshold in an electromagnetic range of the x-ray source;
wherein the configurable sensor has a saturation threshold greater than the saturation threshold of the direct conversion sensor and outputs unsaturated imaging data acquired in an x-ray energy range above the saturation threshold of the direct conversion sensor; and
wherein saturated data in the direct conversion layer is substituted with non-saturated data from a corresponding pixel in the configurable sensor.

16. The diagnostic imaging detector of claim 15 wherein the configurable sensor is further configurable to operate in a photon-counting mode.

17. The diagnostic imaging detector of claim 15 wherein the configurable sensor comprises a photodiode and a scintillator.

18. The diagnostic imaging detector of claim 15 wherein the material of the configurable sensor has an atomic number in a range of about 14 to about 64.

19. The diagnostic imaging detector of claim 15 wherein the configurable sensor has a thickness sufficient to attenuate up to fifty percent of incident photons.

20. The diagnostic imaging detector of claim 15 wherein the direct conversion sensor is configured to attenuate a majority of the photons incident to the detector that pass through the configurable sensor.

* * * * *